United States Patent
Kennedy

(10) Patent No.: US 10,105,269 B1
(45) Date of Patent: Oct. 23, 2018

(54) BABY DIAPER

(71) Applicant: Chandrawatti Kennedy, Jamaica, NY (US)

(72) Inventor: Chandrawatti Kennedy, Jamaica, NY (US)

( * ) Notice: Subject to any disclaimer, the term of this patent is extended or adjusted under 35 U.S.C. 154(b) by 187 days.

(21) Appl. No.: 14/044,310

(22) Filed: Oct. 2, 2013

(51) Int. Cl.
    *A61F 13/15*     (2006.01)
    *A61F 13/49*     (2006.01)
    *A61F 13/56*     (2006.01)

(52) U.S. Cl.
    CPC .... *A61F 13/5638* (2013.01); *A61F 13/15756* (2013.01); *A61F 13/49019* (2013.01)

(58) Field of Classification Search
    CPC .. A61F 2013/49041; A61F 2013/49074; A61F 2013/49076; A61F 2013/49082; A61F 2013/49098; A61F 2013/51095; A61F 2013/5694; A61F 2013/8497
    See application file for complete search history.

(56) References Cited

U.S. PATENT DOCUMENTS

| | | | |
|---|---|---|---|
| 4,500,316 A * | 2/1985 | Damico | A61F 5/4401 |
| | | | 604/385.29 |
| 5,366,453 A | 11/1994 | Zehner et al. | |
| 5,389,438 A * | 2/1995 | Miller | A61F 13/58 |
| | | | 428/355 BL |
| H1440 H * | 5/1995 | New | A61F 5/4401 |
| | | | 604/385.21 |
| 5,593,401 A * | 1/1997 | Sosalla | A61F 13/49011 |
| | | | 604/385.28 |
| 5,685,873 A | 11/1997 | Bruemmer | |
| 5,899,896 A * | 5/1999 | Suprise | A61F 13/62 |
| | | | 604/358 |
| 6,277,106 B1 * | 8/2001 | Boudry | A61F 13/58 |
| | | | 604/385.01 |
| 6,905,488 B2 | 6/2005 | Olson | |
| 7,429,688 B2 * | 9/2008 | Yoshioka | A61F 13/42 |
| | | | 442/118 |
| 7,857,801 B2 | 12/2010 | Hamall et al. | |
| 8,314,284 B1 | 11/2012 | Novello | |
| 2002/0183706 A1 * | 12/2002 | Valentin | A61F 13/49466 |
| | | | 604/385.01 |

(Continued)

FOREIGN PATENT DOCUMENTS

| | | |
|---|---|---|
| EP | 0639362 | 2/1995 |
| EP | 0838205 | 10/2007 |

(Continued)

*Primary Examiner* — Peter S Vasat
(74) *Attorney, Agent, or Firm* — Goldstein Law Offices, P.C.

(57) ABSTRACT

A diaper having an elastic chest band on an extended front portion of a diaper coupled to an elastic upper back band on an extended back portion that prevents bodily waste leaking onto to a wearer's upper torso. The diaper has a pair of wrap around sides. In one example embodiment, the diaper has a pair of absorbent wings coupled to a center panel of the diaper that wrap around a wearer's torso, keeping the diaper snuggly fitting and preventing bodily waste leakage. The diaper has a pair of leg portions that extend down a wearer's thighs, each having a bottom elastic band to prevent leakage down the legs. The diaper has a belt in one example embodiment and an indicator strip in another example embodiment.

13 Claims, 10 Drawing Sheets

(56) References Cited

U.S. PATENT DOCUMENTS

| | | | |
|---|---|---|---|
| 2005/0148982 A1* | 7/2005 | Van Gompel | A61F 13/495 604/385.22 |
| 2005/0222553 A1* | 10/2005 | Crislip Wilkinson | A61F 13/49 604/396 |
| 2008/0168829 A1 | 7/2008 | Paez | |

FOREIGN PATENT DOCUMENTS

| | | |
|---|---|---|
| WO | WO9324085 | 12/1993 |
| WO | WO9501148 | 1/1995 |
| WO | WO2008118713 | 10/2008 |

* cited by examiner

BABY DIAPER

TECHNICAL FIELD

The present disclosure relates generally to a diaper. More particularly, the present disclosure relates to a diaper for preventing leakage of bodily waste.

BACKGROUND

Diapers are primarily for infants to absorb and contain the urine and feces produced by the untoileted infant. As the infant becomes mobile, progressing through the stages of creeper, crawler to toddler, the movements and mobility of the infant and young child challenge the ability of an ordinary diaper to absorb and contain urine and feces, particularly runny or watery bowel movements.

Leaking diapers of a mobile infant and child creates more places where a diaper leak can spread in the home and in public. Young children go to parks, play dates, restaurants, movies, classes and travel on planes, trains, buses and cars, spreading germs and bodily waste through their leaky diapers. Clothes and furniture are soiled or perhaps ruined.

At home, as the baby sits in the high chair or in the car, as the baby sits in a car seat, feces runs up their back, spilling over the top of the diaper. While leaks occur when the baby is having normal bowel movements, the leakage becomes a disgusting situation when the bowel movement is watery and runny.

Leaking diapers are also problematic for adults, particularly those adults who are bedridden. Watery bowel movements can spread out the top of the waistband when the adult is lying in a supine position.

Disposable diapers with elastic leg bands, plastic or rubber pants with elastic leg bands and various forms of cloth diapers have been designed to contain watery and runny bowel movements from seeping out the leg openings.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a diaper that prevents leakage of bodily waste out the diaper top. Accordingly, the present disclosure provides a diaper having an elastic chest band on an extended front portion of a diaper that prevents bodily waste leaking on to a wearer's chest.

Another aspect of an example embodiment in the present disclosure is to provide a diaper that prevents leakage of bodily waste out of a diaper top. Accordingly, the present disclosure provides a diaper having an elastic upper back band on an extended back portion of a diaper that prevents bodily waste leaking on to a wearer's back.

A further aspect of an example embodiment in the present disclosure is to provide a diaper that prevents leakage of bodily waste out of a diaper top by providing a snug fit. Accordingly, the present disclosure provides a pair of absorbent wings coupled to a center panel of a diaper that wrap around a wearer's torso, keeping the diaper snuggly fitting and preventing bodily waste leaking.

Yet another aspect of an example embodiment in the present disclosure is to provide a diaper that prevents leakage of bodily waste from a diaper bottom. Accordingly, the present disclosure provides a pair of leg portions that extend down a wearer's thighs that have a bottom elastic band to prevent leakage of bodily waste from a diaper's bottom.

Accordingly, the present disclosure describes a diaper having an elastic chest band on an extended front portion of a diaper coupled to an elastic upper back band on an extended back portion that prevents bodily waste leaking onto to a wearer's upper torso. The diaper has a pair of wrap around sides. In one example embodiment, the diaper has a pair of absorbent wings coupled to a center panel of the diaper that wrap around a wearer's torso, keeping the diaper snuggly fitting and preventing bodily waste leakage. The diaper has a pair of leg portions that extend down a wearer's thighs, each having a bottom elastic band to prevent leakage down the legs. The diaper has a belt in one example embodiment and an indicator strip in another example embodiment.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
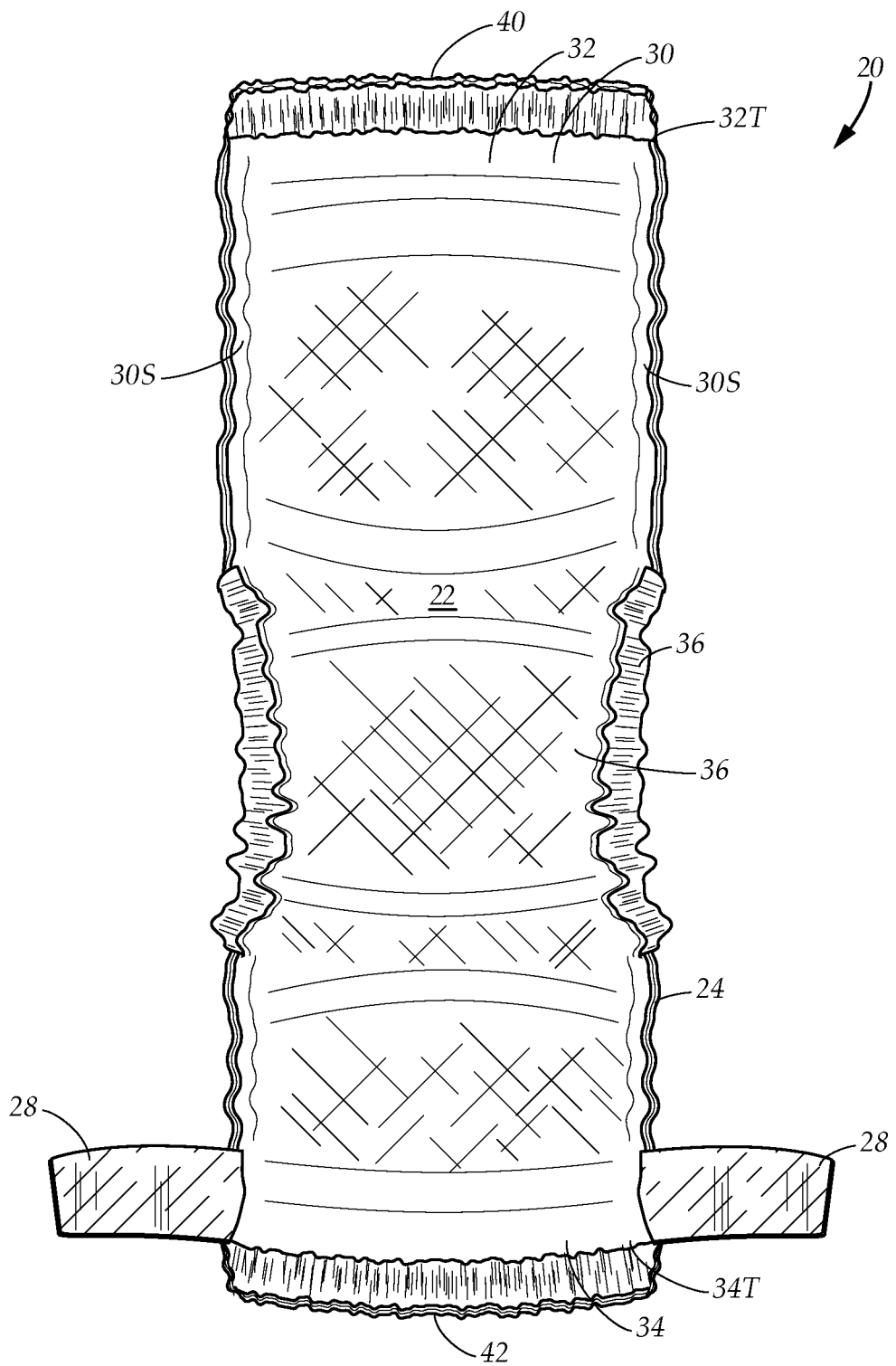
FIG. 1 is a top plan view of a diaper of the present disclosure.

FIG. 1 illustrates a diaper 20 for preventing leakage of bodily waste, especially when a wearer is lying down or when the bodily waste is substantially a voluminous liquid, such as urine or loose watery bowel movements. The diaper prevents leaking out through the diaper top caused by overflowing waste by providing an elongated center panel 30 that extends upwards towards the wearer's chest and upper back.

The center panel 30 has a middle crotch portion 36, an extended front portion 32 that extends from the middle crotch portion 36 to a front top 32T of the diaper. The center panel 30 has an extended back portion 34 that extends from the middle crotch portion 36 to a back top 34T of the diaper. The center panel has opposing sides 30S The center panel has an absorbent material layer 22 on an inner side and an impermeable backing layer 24 on an outer side, the impermeable backing layer covering the absorbent material layer.

The front top 32T has an elastic chest band 40, the chest band operative for wearing across the wearer's chest. The back top 34T has an elastic upper back band 42 operative for wearing across the wearer's upper back.

The diaper has a pair of adhesive tabs 28, a tab on each side of the center panel 30 adjacent to the upper back band 42, the adhesive tab having an interior adhesive coating layer 26 operative for coupling the back portion 34 of the center panel 30 to the front portion 32 of the center panel 30 adjacent to the chest band 40 at the front top 32T of the center panel.

The sides 30S of the center panel each have an elastic leg band 62 at the crotch portion 36 between the front portion and the back portion operative for sealing a leg opening when the diaper is placed on the wearer, the center panel 30 extending between a pair of legs of the wearer.

Figure 2:
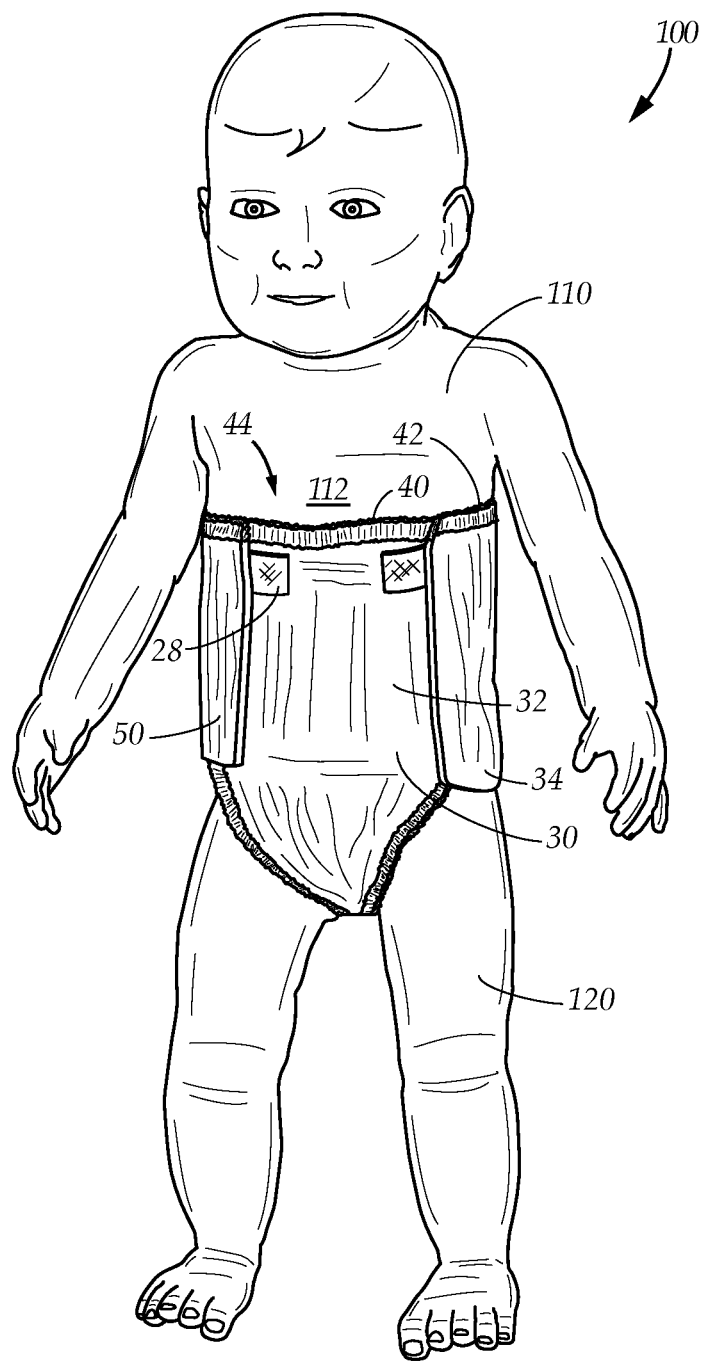
FIG. 2 is a perspective view of an infant wearer from the front, wearing the diaper of the present disclosure.

FIG. 2 shows the diaper 20 on a wearer 100. While the illustrations show the diaper being worn by an infant or toddler, it is understood that the disclosed diaper is useful for adults, such as bedridden adults. The front portion 32 of the center panel extends to an upper torso 110 of the wearer, extending to a chest 112 in front and an upper back in back. The elastic chest band 40 extends across the chest 112. The back portion 34 of the center panel 30 overlaps the front portion 32, the adhesive tabs 28 further coupling the chest band 40 and the upper back band 42 forming an upper torso band 44, the upper torso band 44 operative for sealing the tops 32T, 34T of the center panel 30 when the diaper is placed on the wearer 100. The center panel 30 extends between a pair of legs 120 of the wearer to the front and back of the upper torso 110 of the wearer, the upper torso band 44 operative for preventing leakage of bodily waste on the upper torso of the wearer.

In the illustrated example embodiment in FIG. 2, the back portion 34 of the center panel 30 has a pair of side panels 50, one side panel to each of said sides. The side panels 50 have the layer of absorbent material, which is not visible in the drawing, with the outer layer 24 of impermeable backing material. The side panels 50 overlap the sides of the front portion of the center panel when the adhesive tabs 28 couple the back portion 34 of the center panel to the front portion 32 of the center panel 30.

In one example embodiment, the side panels 50 have an interior layer of low tack adhesive on top of the absorbent layer, the adhesive layer operative for selectively adhering the side panels 50 to the front portion 32 of the center panel 30.

Figure 3:
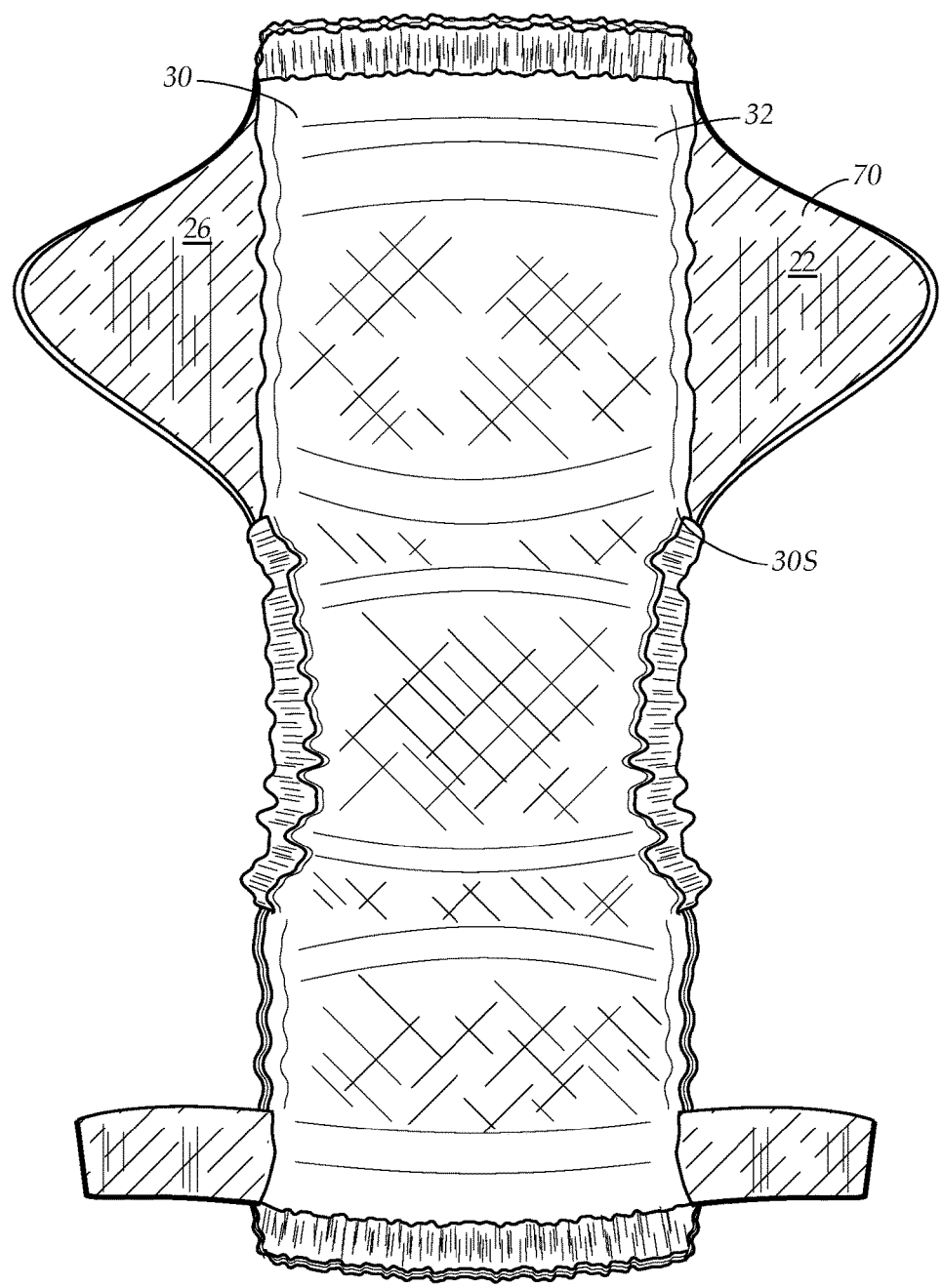
FIG. 3 is a top plan view of another example embodiment of the diaper of the present disclosure.

In another example embodiment shown in FIG. 3, the front portion 32 of the center panel 30 has pair of wing panels 70 coupled to the sides 30S of the front portion, one wing panel 70 to each side. In one example embodiment, the wing panels have a layer of absorbent material 22. In one example embodiment, the wing panels have a layer of low tack adhesive operative 26 for selectively attaching the wing panels to the torso of the wearer. In one example embodiment, the wing panels 70 have a layer of low tack adhesive and a layer of absorbent material.

Figure 4:
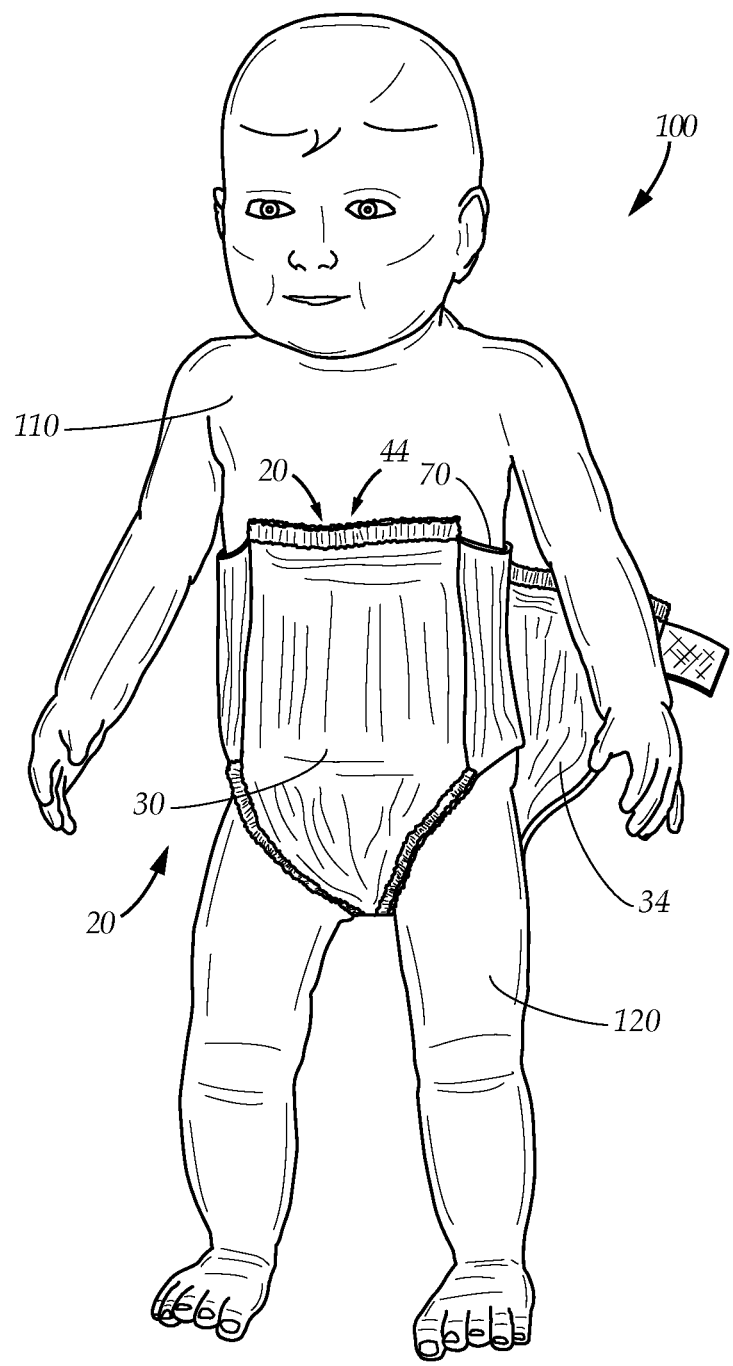
FIG. 4 is a perspective view of the infant wearer from the front, wearing another example embodiment of the diaper of the present disclosure.
Figure 5:
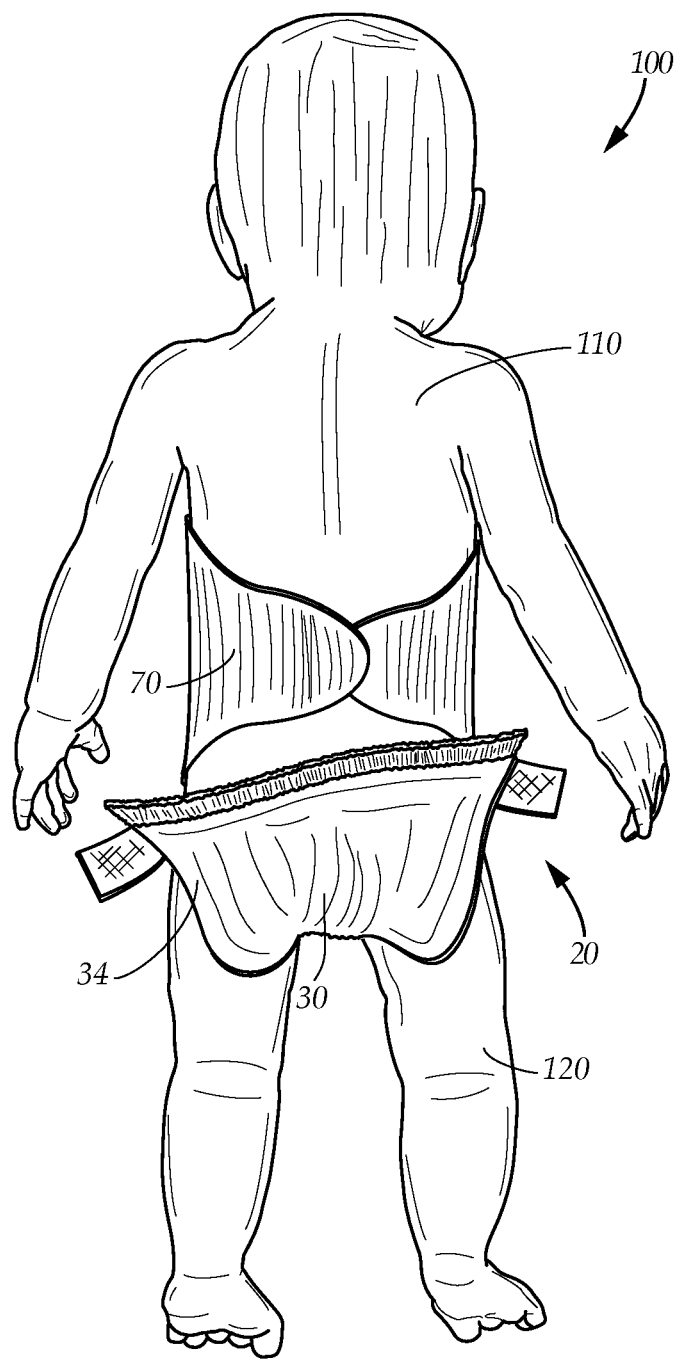
FIG. 5 is a perspective view of the infant wearer from the rear, wearing another example embodiment of the diaper of the present disclosure.

FIG. 4 demonstrates the diaper 20 having the wing panels 70 placed on the wearer 100. In FIG. 5, the wing panels are shown wrapping around a back of the upper torso 110 of the wearer 100 when the diaper 20 is placed on the wearer. Referring to both FIG. 4 and FIG. 5, the center panel 30 extends between the legs 120 of the wearer and the back portion 34 of the center panel 30 covers over the wing panels, the wing panels operative as a barrier for preventing leakage of waste through the top upper torso band 44 of the diaper. The wing panels 70 are operative for creating a snug fit around the upper torso 110.

Figure 7:
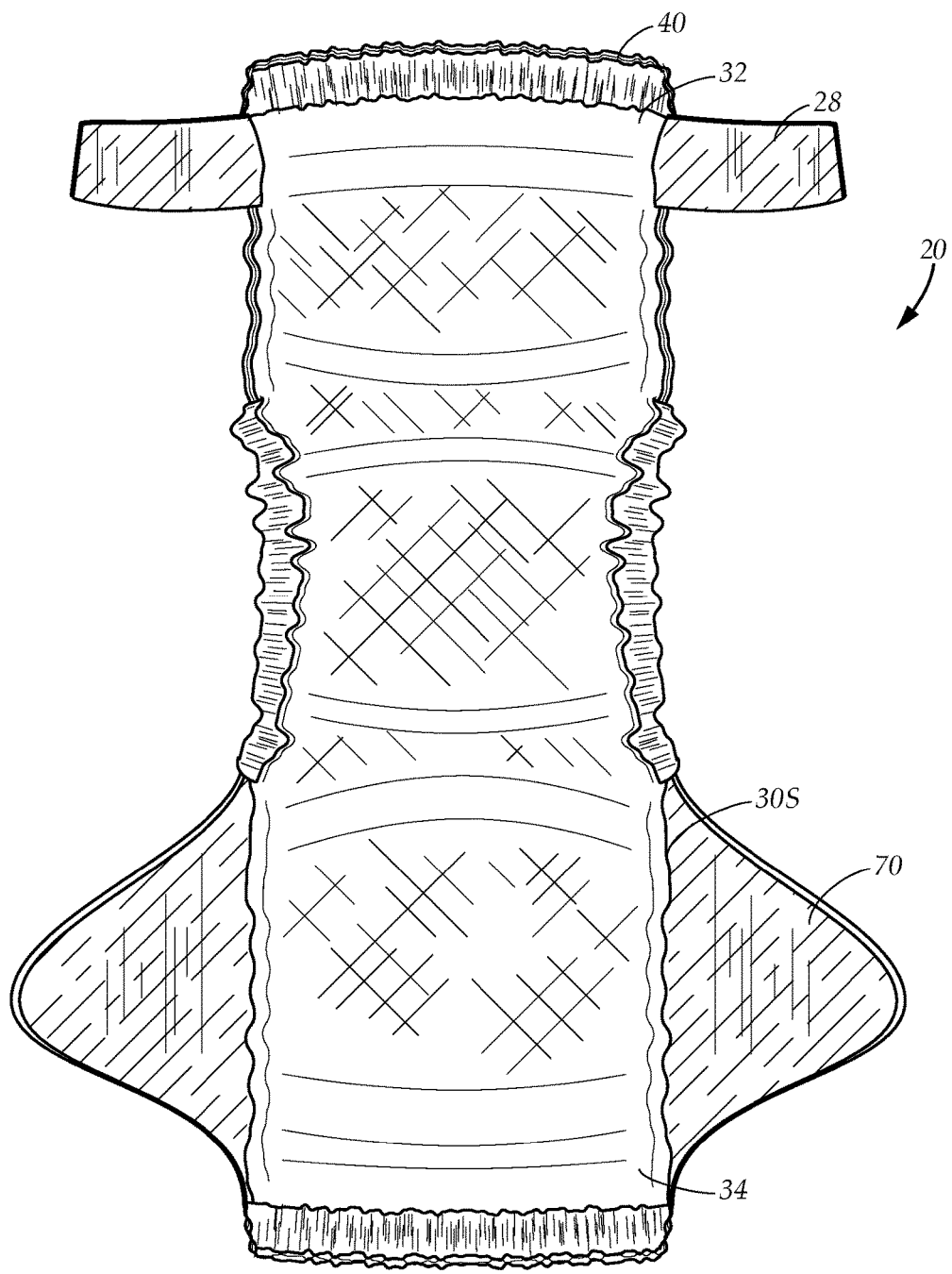
FIG. 7 is a top plan view of yet another example embodiment of the diaper of the present disclosure.
Figure 8:
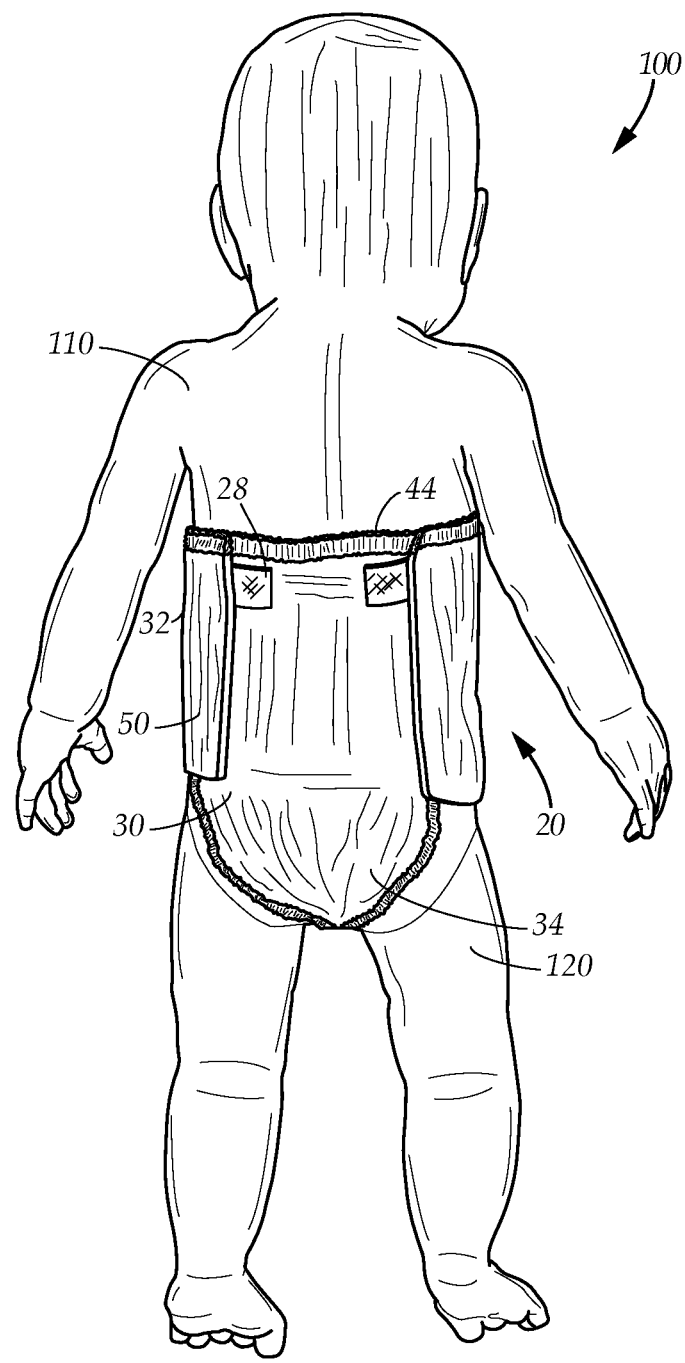
FIG. 8 is a perspective view of the infant wearer from the rear, wearing yet another example embodiment of the diaper of the present disclosure.

FIG. 7 shows yet another example embodiment of the diaper 20. The wing panels 70 are coupled to the sides 30S of the back portion 34, one wing panel to each of the sides and the adhesive tabs 28 are adjacent to the chest band 40 coupled to the front portion 32. FIG. 8 shows this example embodiment on the wearer 100. The wing panels are operative for wrapping around the front of the upper torso 110 of the wearer when the diaper 20 is placed on the wearer 100, the center panel 30 extending between a pair of legs 120 of the wearer, the front portion 32 of the center panel covering over the wing panels, the wing panels operative as a barrier for preventing leakage of waste through the top upper torso band 44 of the diaper. In one example embodiment, the front portion has a pair of side panels coupled to the sides, the side panels 50 overlapping the sides of the back portion 34 of the center panel when the adhesive tabs 28 couple the front portion 32 of the center panel 30 to the back portion 34 of the center panel 30.

As described hereinabove with reference to the side panels coupling to the back portion, the side panels 50 have the layer of absorbent material, which is not visible in the drawing, with the outer layer 24 of impermeable backing material. In one example embodiment, the side panels 50 have an interior layer of low tack adhesive on top of the absorbent layer, the adhesive layer operative for selectively adhering the side panels 50 to the back portion 34 of the center panel 30.

Figure 9:
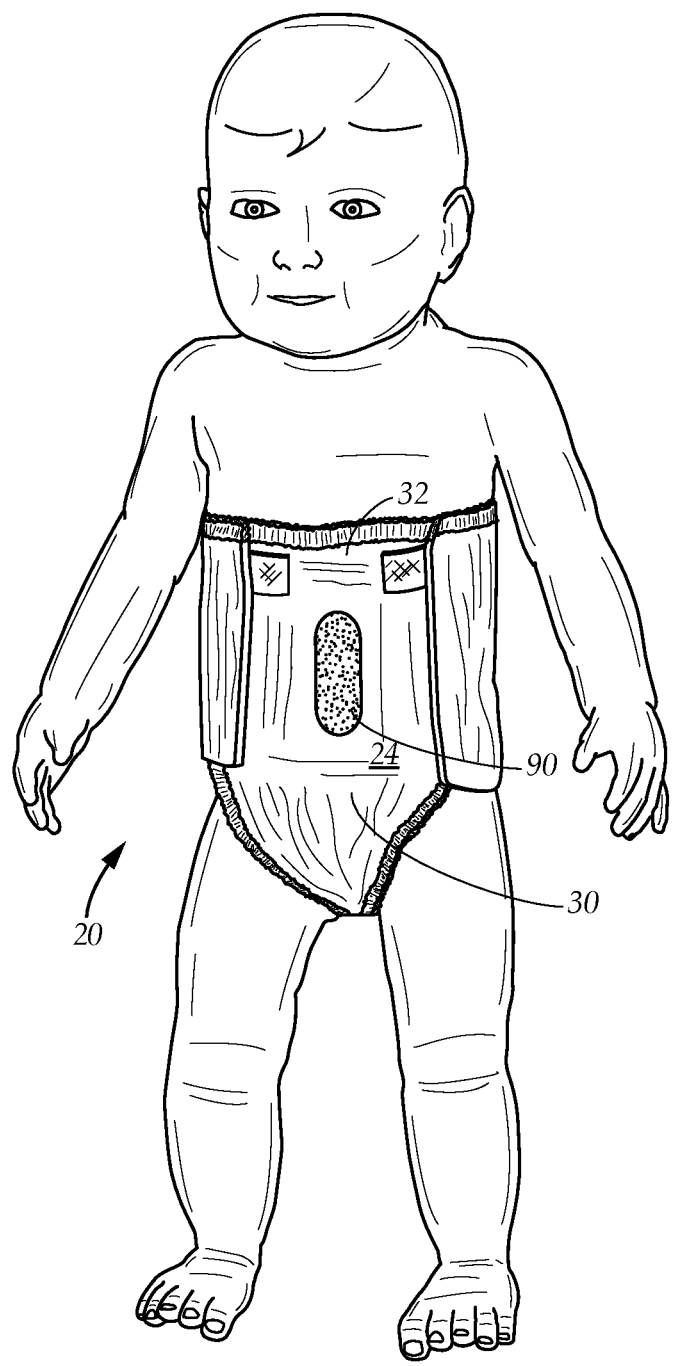
FIG. 9 is a perspective view of the infant wearer from the front, wearing yet a further example embodiment of the diaper of the present disclosure.

FIG. 9 illustrates yet a further example embodiment of the diaper 20. The front portion 32 of the center panel 30 has an indicator strip 90 operative for indicating the absorbent layer of the center panel is wet from bodily waste, the indicator strip visible on the outer impermeable layer 24 of the center panel 30.

Figure 10:
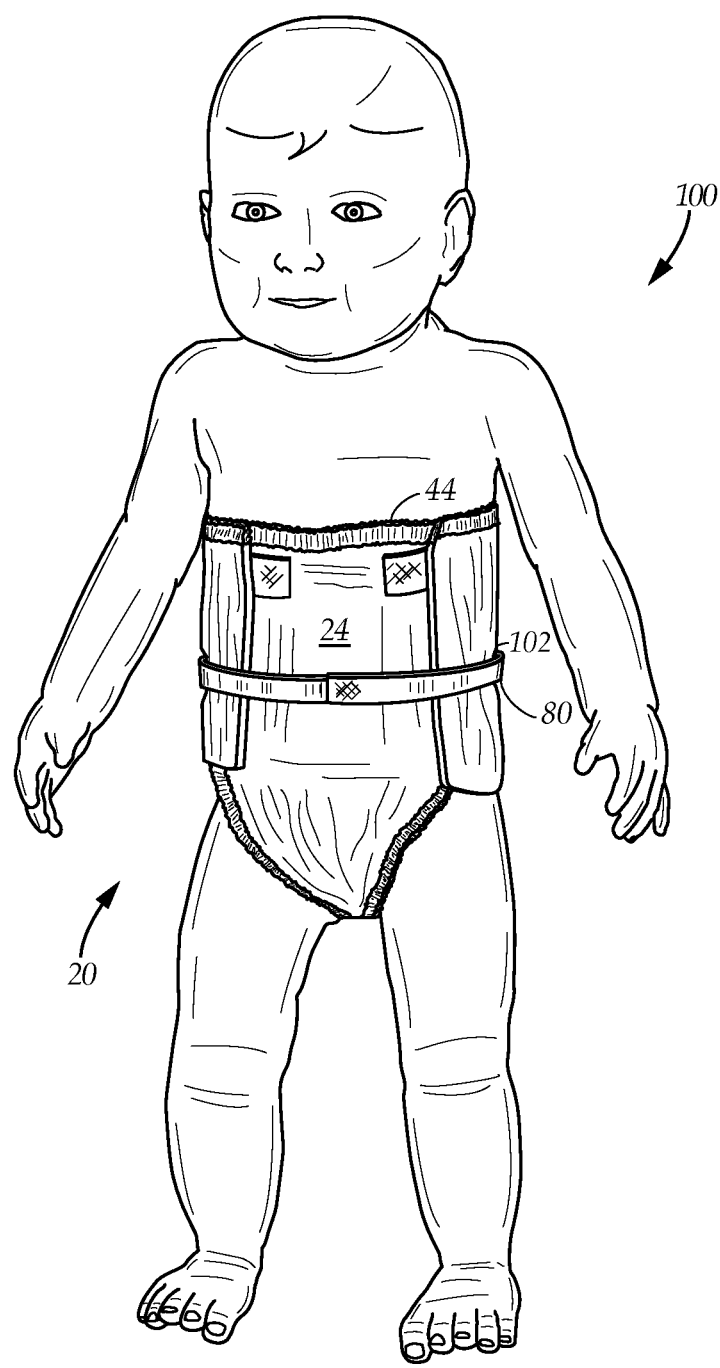
FIG. 10 is a perspective view of the infant wearer from the front, wearing still another example embodiment of the diaper of the present disclosure.

FIG. 10 demonstrates still another example embodiment of the diaper 20. A belt 80 is coupled to the outer impermeable layer 24 and the belt is selectively wrapped around a waist 102 of the wearer 100, the belt operative for creating a further barrier in the diaper for preventing leakage of solid bodily waste through the top upper torso band 44 of the diaper. In one example embodiment, the inner layer of the belt has an adhesive layer coated with a low tack adhesive to keep the belt in place around the waist.

Figure 6:
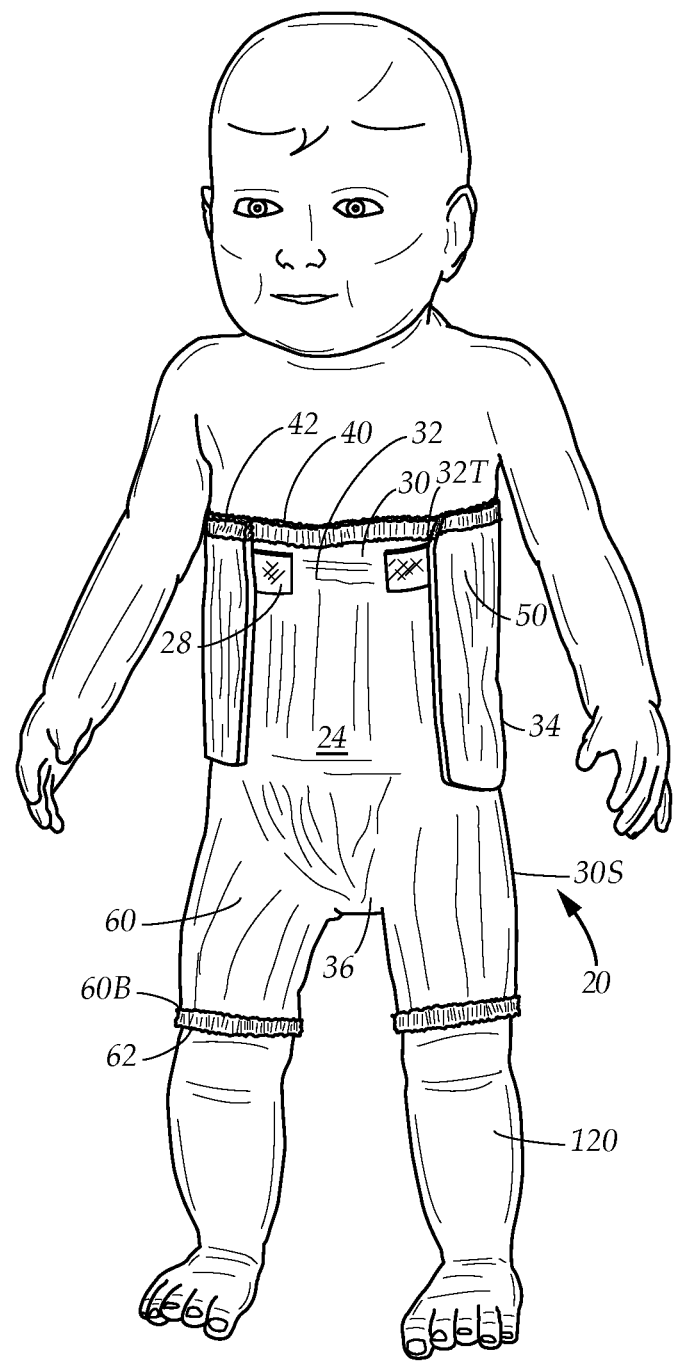
FIG. 6 is a perspective view of the infant wearer from the front, wearing a further example embodiment of the diaper of the present disclosure.

FIG. 6 shows yet a further example embodiment of the diaper 20. The center panel 30 has the extended front portion 32 that extends from the middle crotch portion 36 to a front top 32T of the diaper. The center panel 30 has an extended back portion 34 that extends from the middle crotch portion 36 to a back top of the diaper. The diaper 20 has a pair of leg portions 60 coupled to the center panel, a leg portion coupled to each opposing side 30S of the center panel, the leg portion 60 having a bottom 60B with an elastic leg band 62.

The center panel 30 has an absorbent material layer 22 on an inner side and an impermeable backing layer 24 on an outer side, the impermeable backing layer covering the absorbent material layer.

The front top 32T has an elastic chest band 40 the chest band operative for wearing across the wearer's chest. The back top 34T has an elastic upper back band 42 operative for wearing across the wearer's upper back.

The diaper has a pair of adhesive tabs 28, a tab on each side of the center panel 30 adjacent to the upper back band 42, the adhesive tab having an interior adhesive coating layer operative for coupling the back portion 34 of the center panel 30 to the front portion 32 of the center panel 30 adjacent to the chest band 40 at the front top 32T of the center panel.

The back portion 34 of the center panel 30 has a pair of side panels 50, one side panel to each sides. The side panels 50 have the layer of absorbent material, which is not visible in the drawing, with the outer layer 24 of impermeable backing material. The side panels 50 overlap the sides of the front portion of the center panel when the adhesive tabs 28 couple the back portion 34 of the center panel to the front portion 32 of the center panel 30.

In one example embodiment, the side panels 50 have an interior layer of low tack adhesive on top of the absorbent layer, the adhesive layer operative for selectively adhering the side panels 50 to the front portion 32 of the center panel 30.

As described hereinabove, the example embodiment can include the wing panels, which are not shown, coupled to the sides of the front portion. The wing panels comprise a layer of absorbent material and an interior layer of low tack adhesive.

While not shown, another example embodiment includes the leg portions as drawn in FIG. 6 and the indicator strip as described hereinabove. Another example embodiment includes the leg portions and the belt as described hereinabove.

A method of making a diaper for preventing leakage of bodily waste as shown in FIG. 1 comprises coupling the elastic chest band 40 and the elastic upper back band 42 to the center panel 30 having a layer of absorbent material 22 with an exterior layer of impermeable backing material. The center panel 30 has an extended front portion 32 with a front top 32T and an extended back portion 34 with a back top 34T and opposing sides. The elastic chest band 40 couples to the front top 32T of the front portion 32 of the center panel, and the elastic upper back band 34 couples to the back top 34T of the back portion 34 of the center panel.

The adhesive tabs 28 couple to each center panel side 30S adjacent to the upper back band 34, the adhesive tabs having an interior adhesive coating, the adhesive tabs further coupling the chest band 40 and the upper back band 42 forming the upper torso band 44.

The method of making the diaper as illustrated in FIG. 2 further comprises coupling a pair of side panels 50 to the back portion 34 of the center panel, one side panel to each side. The method of making the diaper as illustrated in FIG. 3 further comprises coupling a pair of wing panels 70 to the sides of the front portion 32, one wing panel to each side.

The method of making the diaper 20 as illustrated in FIG. 10 further comprises coupling the belt 80 to the exterior impermeable layer 24 of the center panel.

The method of making the diaper 20 as illustrated in FIG. 9 further comprises coupling the indicator strip 90 operative for indicating the absorbent layer of the center panel is wet from bodily waste to front portion 32 of the center panel 30.

The method of making the diaper 20 as illustrated in FIG. 6 further comprises coupling a pair of leg portions to said center panel, a leg portion 60 coupled to each opposing side 30S of the center panel 30, the leg portion 60 having a bottom 60B with an elastic leg band 62.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a diaper for preventing leakage of bodily waste. The disclosure is illustrated by example in the drawing figures, and throughout the written description. It should be understood that numerous variations are possible, while adhering to the inventive concept. Such variations are contemplated as being a part of the present disclosure.

What is claimed is:

1. A diaper for preventing leakage of bodily waste, comprising:
    a center panel having a layer of absorbent material with an outer layer of impermeable backing material, said center panel having an extended front portion with a front top, said center panel having an extended back portion with a back top, said center panel having a middle crotch portion positioned centrally between the front portion and the back portion, said center panel having opposing sides;
    an elastic chest band on the front top of the front portion of said center panel;
    an elastic upper back band on the back top of the back portion of said center panel; and
    a pair of adhesive tabs, a tab on each side of said center panel adjacent to the upper back band and having a common border with the upper back band at least at a connection point of the tab with the said center panel, the adhesive tab having an interior adhesive coating layer operative for coupling the back portion of said center panel to the front portion of said center panel adjacent to the chest band at the top of said front portion of said center panel, the back portion overlapping the front portion, the adhesive tabs further coupling the chest band and the upper back band;
    a pair of wing panels coupled to the front portion of said center panel, a wing panel positioned on each side of said center panel substantially midway between the middle crotch portion and the chest band, one wing panel to each of said sides, the wing panels operative for wrapping entirely around an upper torso of a wearer when the diaper is placed on the wearer, the wing panels operative to overlap each other at a back of the upper torso of the wearer when the diaper is placed on the wearer, the back portion of said center panel entirely covering over the wing panels when the diaper is placed on the wearer;
    an upper torso band, formed when the chest band couples to the upper back band, the upper torso band operative for sealing the tops of said center panel when the diaper is placed on a wearer, the center panel adapted to extend between a pair of legs of the wearer to the upper torso of the wearer, the middle crotch portion adapted to cover a crotch of the wearer, the upper torso band operative for preventing leakage of bodily waste on the upper torso of the wearer; and
    wherein the wing panels are absorbent and are operative as a barrier for preventing leakage of waste through the upper torso band of the diaper.

2. The diaper as described in claim 1, wherein the back portion of said center panel includes a pair of side panels, one side panel to each of said opposing sides, said side panels having the layer of absorbent material with the outer layer of impermeable backing material, the side panels overlapping the sides of the front portion of said center panel with the adhesive tabs adapted to couple the back portion of said center panel to the front portion of said center panel.

3. The diaper as described in claim 2, wherein the side panel has an interior layer of low tack adhesive operative for selectively adhering the side panels to the front portion of said center panel.

4. The diaper as described in claim 1, wherein the wing panels comprise an interior layer of low tack adhesive operative for selectively attaching the wing panels to the torso of the wearer.

5. The diaper as described in claim 1, wherein the sides of said center panel each have an elastic leg band between the said front portion and said back portion operative for sealing a leg opening when the diaper is placed on the wearer, the center panel adapted to extend between a pair of legs of the wearer.

6. The diaper as described in claim 1, wherein said front portion of the center panel has an indicator strip operative for indicating the absorbent layer of the center panel is wet from bodily waste, the indicator strip visible on the outer layer of said center panel.

7. The diaper as described in claim 1, wherein a belt is coupled to the outer impermeable layer, the belt adapted to be selectively wrapped around a waist of a wearer, the belt operative for creating a further barrier for preventing leakage of solid bodily waste through the top upper torso band of the diaper.

8. The diaper as described in claim 1, wherein the pair of wing panels extend along the sides of the front portion of said center panel from the chest band to the middle crotch portion.

9. A diaper for preventing leakage of bodily waste, comprising:
    a center panel having a layer of absorbent material with an outer layer of impermeable backing material, said center panel having a front portion with a front top, said center panel having a middle crotch portion positioned centrally between the front portion and the back portion, said center panel having a back portion with a back top and said center panel having opposing sides;
    an elastic chest band on the front top of the front portion of said center panel;
    an elastic upper back band on the back top of the back portion of said center panel;
    a pair of leg portions coupled to said center panel, a leg portion coupled to each opposing side of said center panel, said leg portion having a bottom with an elastic leg band; and
    a pair of adhesive tabs, a tab on each side of said center panel adjacent to the upper back band and having a common border with the upper back band at least at a connection point of the tab with the said center panel, the adhesive tab having an inner adhesive coating operative for coupling the back portion of said center panel to the front portion of said center panel adjacent to the chest band at the top of said front portion of said center panel, the back portion overlapping the front portion, the adhesive tabs further coupling the chest band and the upper back band;

a pair of wing panels coupled to the front portion of said center panel, a wing panel positioned on each side of said center panel substantially midway between the middle crotch portion and the chest band, one wing panel to each of said sides, the wing panels operative for wrapping entirely around an upper torso of a wearer when the diaper is placed on the wearer, the wing panels operative to overlap each other at a back of the upper torso of the wearer when the diaper is placed on the wearer, the back portion of said center panel entirely covering over the wing panels when the diaper is placed on the wearer, the wing panels operative as a barrier for preventing leakage of waste through an upper torso band of the diaper;

an upper torso band, formed when the chest band couples to the upper back band, the upper torso band operative for sealing the tops of said center panel when the diaper is placed on a wearer, the center panel adapted to extend between a pair of legs of the wearer to the upper torso of the wearer, the upper torso band operative for preventing leakage of bodily waste on the upper torso of the wearer; and wherein the wing panels are absorbent and are operative as a barrier for preventing leakage of waste through the upper torso band of the diaper.

10. The diaper as described in claim 9, wherein the back portion of said center panel has a pair of side panels, one side panel to each of said opposing sides, said side panels having the layer of absorbent material with the outer layer of impermeable backing material, the side panels overlapping the sides of the front portion of said center panel with the adhesive tabs adapted to couple the back portion of said center portion to the front portion of said center panel.

11. A diaper for preventing leakage of bodily waste, comprising:

a center panel having a layer of absorbent material with an outer layer of impermeable backing material, said center panel having an extended front portion with a front top, said center panel having an extended back portion with a back top, said center panel having a middle crotch portion positioned centrally between the front portion and the back portion, said center panel having opposing sides;

an elastic chest band on the front top of the front portion of said center panel;

an elastic upper back band on the back top of the back portion of said center panel; and a pair of adhesive tabs, a tab on each side of said center panel adjacent to the chest band and having a common border with the chest band at least at a connection point of the tab with the said center panel, the adhesive tab having an interior adhesive coating layer operative for coupling the front portion of said center panel to the back portion of said center panel adjacent to the upper back band at the top of said back portion of said center panel, the front portion overlapping the back portion, the adhesive tabs further coupling the chest band and the upper back band;

a pair of wing panels coupled to the back portion of said center panel, a wing panel positioned on each side of said center panel substantially midway between the middle crotch portion and the upper back band, one wing panel to each of said sides, the wing panels operative for wrapping entirely around an upper torso of a wearer when the diaper is placed on the wearer, the wing panels operative to overlap each other at a front of the upper torso of the wearer when the diaper is placed on the wearer, the front portion of said center panel entirely covering over the wing panels when the diaper is placed on the wearer;

an upper torso band, formed when the chest band couples to the upper back band, the upper torso band operative for sealing the tops of said center panel when the diaper is placed on a wearer, the center panel adapted to extend between a pair of legs of the wearer to the upper torso of the wearer, the middle crotch portion adapted to cover a crotch of the wearer, the upper torso band operative for preventing leakage of bodily waste on the upper torso of the wearer;

wherein the wing panels are absorbent and are operative as a barrier for preventing leakage of waste through the upper torso band of the diaper.

12. The diaper as described in claim 11, wherein the pair of wing panels extend along the sides of the back portion of said center panel from the upper back band to the middle crotch portion.

13. The diaper as described in claim 12, wherein the wing panels comprise an interior layer of low tack adhesive operative for selectively attaching the wing panels to the torso of the wearer.

* * * * *